United States Patent [19]

Von Der Saal et al.

[11] Patent Number: 5,824,679
[45] Date of Patent: Oct. 20, 1998

[54] PHOSPHANOXIDES—PREPARATION AND USE

[75] Inventors: Wolfgang Von Der Saal, Weinheim; Herbert Leinert; Karlheinz Stegmeier, both of Heppenheim, all of Germany

[73] Assignee: Boehringer Mannheim GmbH, Mannheim, Germany

[21] Appl. No.: 793,446

[22] PCT Filed: Aug. 26, 1995

[86] PCT No.: PCT/EP95/03382

§ 371 Date: Feb. 28, 1997

§ 102(e) Date: Feb. 28, 1997

[87] PCT Pub. No.: WO96/06849

PCT Pub. Date: Mar. 7, 1996

[30] Foreign Application Priority Data

Aug. 30, 1994 [DE] Germany ............... 44 30 755.1

[51] Int. Cl.[6] ............... A61K 31/535; A01N 43/58; C07D 401/00; C07D 211/68
[52] U.S. Cl. ............... 514/252; 514/236; 544/238; 546/194; 546/196
[58] Field of Search ............... 544/238; 546/194, 546/196; 514/252, 236

[56] References Cited

U.S. PATENT DOCUMENTS

| 5,684,151 | 11/1997 | Combs | 544/224 |
| 5,728,702 | 3/1998 | Tanikawa et al. | 514/253 |

FOREIGN PATENT DOCUMENTS

| 555824 | 8/1993 | European Pat. Off. . |
| 43-06-506 A1 | 9/1994 | Germany . |
| 4306506 | 9/1994 | Germany . |
| 94-20467 | 9/1994 | WIPO . |

*Primary Examiner*—Mukund J. Shah
*Assistant Examiner*—Tamthom T. Ngo
*Attorney, Agent, or Firm*—Nikaido, Marmelstein, Murray & Oram LLP

[57] ABSTRACT

The invention concerns novel phosphanoxides of formula 1 in which $R^1$ means aryl or heteroaryl group. The invention further concern the optically active forms, racemates and diastereomers mixtures of these compounds, a method of preparing them and pharmaceutical compositions containing these compounds, and methods of use to produce a thrombin-inhibiting effect.

15 Claims, No Drawings

PHOSPHANOXIDES— PREPARATION AND USE

This is a 371 application of PCT/EP 95/03382 filed on Aug. 26, 1995.

The invention concerns new phosphanoxides of the general formula I

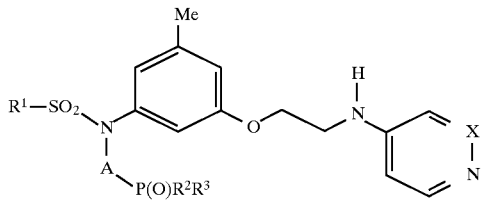

in which
- $R^1$ denotes an aryl or heteroaryl group in which the aryl or heteroaryl residues can be substituted once or several times by nitro, halogen, nitrile, hydroxy, carboxy, alkoxycarbonyl, phenylalkoxycarbonyl, phenyl, alkyl, trifluoromethyl, alkoxy, alkenyloxy, alkinyloxy, aralkyloxy, alkylthio, alkylsufinyl, alkylsulfonyl, amino, alkylamino, dialkylamino, aralkylamino, di-aralkylamino, alkylsulfonylamino, alkylcarbonylamino, formyl amino, carbamoyl, thiocarbamoyl, alkylaminocarbonyl, dialkylaminocarbonyl or alkoxycarbonylalkyloxy,
- $R^2$ and $R^3$ are the same or different and denote straight-chain or branched alkyl groups,
- A denotes a straight-chain or branched alkylene residue,
- X denotes a —CH group or a nitrogen atom, as well as hydrates, solvates and physiologically tolerated salts thereof. The invention also concerns the optically active forms, racemates and mixtures of diastereomers of these compounds.

The invention also concerns processes for the production of the above-mentioned compounds, pharmaceutical agents that contain such compounds as well as the use of these compounds in the production of pharmaceutical agents.

The compounds of the general formula I, their solvates and their salts inhibit thrombin-induced coagulation of fibrinogen in blood as well as thrombin-induced aggregation of blood platelets. Thus they prevent formation of hyaline thrombi and platelet-rich thrombi and can be used to combat and prevent diseases such as thrombosis, apoplexy, coronary infarction, inflammations and arteriosclerosis. Furthermore these compounds have an effect on tumour cells and prevent formation of metastases. As a result they can be used as anti-tumour agents.

Thrombin, the last enzyme of the coagulation cascade, cleaves fibrinogen to form fibrin which is cross-linked by factor XIIIa and becomes an insoluble gel which forms the matrix for a thrombus. Thrombin activates platelet aggregation by proteolysis of its receptor on the blood platelets and in this way also contributes to thrombus formation. When a blood vessel is damaged these processes are necessary in order to stop bleeding. No measurable thrombin concentrations are present in blood plasma under normal conditions. Increases in the thrombin concentration can lead to the formation of thrombi and hence to thromboembolic diseases which occur very frequently especially in industrial countries.

Thrombin is kept ready in plasma in the form of prothrombin and is released from it by factor Xa. Thrombin activates the factors V, VIII and XI by which means factor X is then converted into factor Xa. By this means thrombin catalyzes its own release which is why very rapid increases in thrombin concentrations can occur.

Thrombin inhibitors can therefore inhibit the release of thrombin, the platelet-induced and plasmatic blood coagulation.

There is a whole series of serine proteases apart from thrombin that cleave peptide substrates next to a basic amino acid. In order to limit side-effects, the thrombin inhibitors should be selective i.e. they should inhibit other serine proteases only slightly or not at all. Trypsin in particular being the least specific serine protease, can be easily inhibited by the various inhibitors. Trypsin inhibition can lead to pancreatic stimulation and to pancreatic hypertrophy (J. D. Geratz, Am. J. Physiol. 216, (1969) p. 812).

Plasma contains the protein plasminogen which is converted into plasmin by activators. Plasmin is a proteolytic enzyme whose activity is similar to that of trypsin. It serves to dissolve thrombi by degrading fibrin. Inhibition of plasmin would thus have the opposite effect to that which one would like to achieve by inhibiting thrombin.

Synthetic thrombin inhibitors have already been known for a long time. Substances of the (D)-Phe-Pro-Arg type were synthesized from fibrinogen the natural substrate of thrombin. Such tripeptides imitate the amino acid sequence before the cleavage site on fibrinogen. In order to obtain good inhibitors the carboxylate group of the arginine was changed in such a way that the hydroxy group of serine 195 in the active site of thrombin can react with it. This can for example also be achieved by replacing the carboxylate group by an aldehyde group. Corresponding (D)-Phe-Pro-arginals are described in the Patent Application EP-A 185390.

Benzamidine, a known trypsin inhibitor, was used as the basis for a second group of thrombin inhibitors. The inhibitors obtained in this way not only differ from the (D)-Phe-Pro-Arg types in their chemical structure but also in the way they inhibit: serine 195 of thrombin does not bind to these inhibitors. This clearly follows from X-ray examinations of the structure (W. Bode, D. Turk, J. Stürzebecher, Eur. J. Biochem. 193, 175–182 (1990)). Nα-(2-naphthylsulfonylglycyl)-4-amidino-(R,S)-phenylalanine-piperidide ("NAPAP", DD 235866) belongs to this second class of thrombin inhibitors.

It was surprisingly found that compounds of the general formula I, which have no structures in common with the known thrombin inhibitors, are selective thrombin inhibitors.

If $R^1$ in the general formula I denotes an aryl group then this is understood as a phenyl and naphthyl group. A heteroaryl residue is understood for $R^1$ as monocyclic, bicyclic and tricyclic aromatics with heteroatoms such as nitrogen, oxygen or sulphur preferably furan, thiophene, pyrrole, oxazole, isoxazole, thiazole, isothiazole, imidazole, pyrazole, triazole, tetrazole, pyridine, pyrazine, pyrimidine, pyridazine, triazine, tetrazine, benzothiophene, dibenzothiophene, benzimidazole, carbazole, benzofuran, benzofurazan, benzo-2,1,3-thiadiazole, quinoline, isoquinoline, quinazoline.

Halogens as substituents of aryl or heteroaryl residues denote chlorine, bromine and iodine atoms, but preferably fluorine atoms.

Alkoxycarbonyl groups as substituents of the aryl or heteroaryl residues contain straight-chain or branched alkyl chains with 1 to 6 carbon atoms. Methoxycarbonyl and ethoxycarbonyl groups are preferred.

Phenylalkoxycarbonyl groups as substituents of aryl or heteroaryl residues contain a phenyl group linked to a $C_1$–$C_6$ alkyl chain. In this case a benzyloxycarbonyl group is preferred.

Alkyl groups as substituents of aryl or heteroaryl residues are straight-chained or branched and contain 1 to 6 carbon atoms. A methyl, ethyl, propyl, butyl, pentyl and hexyl group are preferred.

Alkoxy groups as substituents of aryl or heteroaryl residues contain 1 to 6 carbon atoms and are straight-chained or branched. A methoxy, ethoxy, n-propyloxy, i-propyloxy, n-butyloxy, i-butyloxy, tert.-butyloxy, pentyloxy and a hexyloxy group are preferred.

If $R^1$ in the general formula I denotes an aryl or heteroaryl group substituted by an alkenyloxy residue then these are understood as straight-chain or branched residues with 3 to 6 carbon atoms preferably an allyloxy group.

If $R^1$ in the general formula I denotes an aryl or heteroaryl group substituted by an alkinyloxy residue then these are understood as straight-chain or branched residues with 1 to 6 carbon atoms preferably a propargyloxy group.

If $R^1$ in the general formula I denotes an aryl or heteroaryl group substituted by an aralkyloxy residue then this is preferably a benzyloxy residue.

If $R^1$ in the general formula I denotes an aryl or heteroaryl group substituted by an alkylthio, alkylsulfinyl or alkylsulfonyl residue then these are understood as straight-chain or branched residues with 1 to 6 carbon atoms preferably a methylthio, methylsulfinyl or a methylsulfonyl group.

If $R^1$ in the general formula I denotes an aryl or heteroaryl group substituted by an alkylamino or dialkylamino residue then these are understood as straight-chain or branched residues with 1 to 6 carbon atoms preferably a methlyamino, dimethylamino and diethylamino group.

If $R^1$ in the general formula I denotes an aralkylamino residue or a di-aralkylamino residue then a benzylamino group and a bis(benzyl)amino group are particularly preferred.

If $R^1$ in the general formula I denotes an aryl or heteroaryl group substituted by an alkylsulfonylamino residue then these are understood as straight-chain or branched residues with 1 to 6 carbon atoms preferably a methlysulfonylamino group.

If $R^1$ in the general formula I denotes an aryl or heteroaryl group substituted by an alkylcarbonylamino residue then these are understood as straight-chain or branched residues with 1 to 6 carbon atoms preferably an acetylamino group.

If $R^1$ in the general formula I denotes an aryl or heteroaryl group substituted by an alkylaminocarbonyl or dialkylaminocarbonyl residue then these are understood as straight-chain or branched residues with 1 to 6 carbon atoms preferably a methylaminocarbonyl, dimethylaminocarbonyl or diethylaminocarbonyl group.

If $R^1$ in the general formula I denotes an aryl or heteroaryl group substituted by an alkoxycarbonylalkyloxy residue then an ethoxycarbonylmethyloxy group is especially preferred.

In the general formula I the alkyl groups for $R^2$ and $R^3$ are understood as straight-chain or branched residues with 1 to 6 carbon atoms such as a methyl, ethyl, propyl, butyl, pentyl and hexyl group.

In the general formula I alkylene groups for A are understood as straight-chain or branched residues with 1 to 6 carbon atoms such as a methylene, ethylene, propylene, butylene, pentylene and hexylene group.

In particular $R^1$ is an unsubstituted phenyl group or a phenyl group substituted once or several times by $C_1$–$C_6$ alkoxy groups (such as e.g. methoxy, propyloxy, butoxy or hexyloxy).

$R^2$ and $R^3$ are in particular the same and denote $C_1$–$C_6$ alkyl groups (such as a methyl group), A is especially a $C_1$–$C_6$ alkylene group (such as a methylene group).

Compounds of the general formula I are preferred

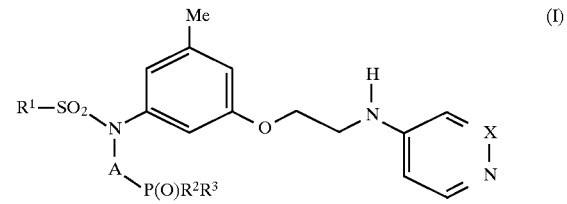

in which
 $R^1$ denotes an unsubstituted phenyl group or a phenyl group substituted by a methoxy, ethoxy, propyloxy, isopropyloxy, butoxy or hexyloxy group,
 $R^2$ and $R^3$ are the same and denote methyl groups,
 A denotes a methylene group
 X denotes a —CH group and a nitrogen atom.

Compounds of the general formula I can be produced by well-known methods.

The compounds of the general formula II

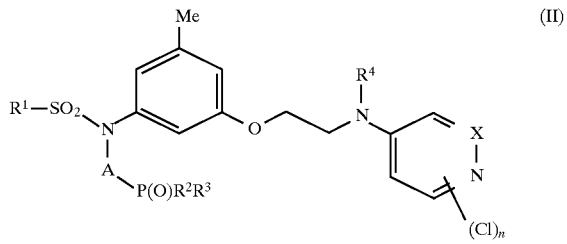

in which $R^1$, $R^2$, $R^3$, A and X have the above-mentioned meanings are hydrogenated. $R^4$ denotes a hydrogen atom or a benzyl group. In the case that X denotes a —CH group, n=4. In the case that X denotes a nitrogen atom, n=2. The hydrogenation is carried out in an inert solvent such as methanol or ethanol in the presence of a catalyst such as palladium on carbon or Raney nickel and in the presence of a base such as N-methylmorpholine, triethylamine, potassium carbonate, sodium bicarbonate or sodium methylate preferably at normal pressure and room temperature. The hydrogenation can also be achieved in the absence of a base. In the case that $R^4$ denotes a benzyl group this can be removed if desired even before the hydrogenation. This can be achieved by reaction with a strong acid such as trifluoroacetic acid in the presence of mesitylene, anisol or thioanisol.

Compounds of the general formula II are produced by reacting compounds of the general formula III with the phosphanoxides of the general formula IV.

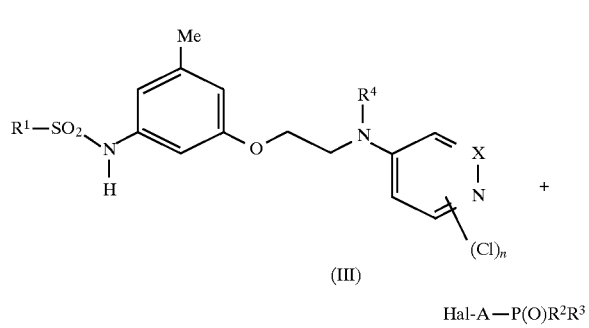

In the general formula III $R^1$, $R^4$ and n have the meanings stated above. In the general formula IV $R^2$, $R^3$ and A have the meanings given above and Hal denotes a halogen atom preferably a chlorine atom. The reaction is carried out in an inert solvent or without solvent in a melted mixture of compounds III and IV and a base such as sodium hydride or potassium carbonate at temperatures between 100° and 200° C.

The compounds of the general formula IV are known from the literature or are commercially available.

A preferred process for producing compounds of the general formula III is to react amines of the general formula V $$R^1-SO_2\underset{H}{N}-\underset{Me}{\overset{}{\bigcirc}}-O-CH_2CH_2-NHR^4 \quad V$$

in which $R^1$ and $R^4$ have the meanings given above with pentachloropyridine or 4-nitrotetrachloropyridine in the process of which compounds of the general formula III are formed in which X denotes a —CH group or with 3,4,5-trichloropyridazine to form compounds of the general formula III in which X denotes a nitrogen atom. This reaction is carried out in an inert solvent such as ethanol, toluene, tetrahydrofuran or dimethylformamide at temperatures between 0° and 100° C. in the presence of a base such as triethylamine, N-methylmorpholine or potassium carbonate.

The compounds of the general formula V are obtained from compounds of the general formula VI $$R^1-SO_2\underset{H}{N}-\underset{Me}{\overset{}{\bigcirc}}-O-R^5 \quad VI$$

in which $R^1$ has the meanings given above and $R^5$ is a nitrile group —CN, an amide group —CONH$_2$ or a phthalimidomethyl group. The aminomethyl group is released from the residue $R^5$ in a well-known manner. In the case that $R^5$ denotes a nitrile group this is achieved by hydrogenation in the presence of a catalyst such as Raney nickel or palladium on carbon or by reduction with lithium aluminium hydride or lithium borohydride in the presence of trimethylsilyl chloride. In the case that $R^5$ denotes an amide group this is achieved by reduction with lithium aluminium hydride or lithium borohydride in the presence of trimethylsilyl chloride. In the case that $R^5$ denotes a phthalimidomethyl group this is achieved by an acid such as hydrochloric acid or by a base such as sodium hydroxide solution or potassium hydroxide solution or by the action of hydrazine hydrate. In this way compounds of the general formula V are firstly formed in which $R^4$ denotes a hydrogen atom. Optionally compounds of the general formula V can be produced therefrom in which $R^4$ denotes a benzyl group. This is achieved by reductive amination by reacting amines of the general formula V with benzaldehyde in an inert solvent such as toluene in the presence of catalytic amounts of an acid such as toluene-4-sulfonic acid and subsequently with sodium borohydride.

The compounds of the general formula VI are obtained by reacting compounds of the general formula VII $$H_2N-\underset{Me}{\overset{}{\bigcirc}}-O-R^5 \quad VII$$

in which $R^5$ has the meanings given above with sulfonic acid chlorides $R^1$—SO$_2$Cl in which $R^1$ has the meanings stated above. It is expedient to carry out the reaction with the addition of an acid-binding agent such as e.g. alkali acetate, alkali hydroxide, calcium oxide, calcium carbonate, magnesium carbonate or with organic bases such as pyridine, triethylamine, N-methylmorpholine or di-isopropylethylamine in which case ether, methylene chloride, dioxane, toluene or an excess of the tertiary amine serve for example as an inert solvent. Water or aqueous ethanol is for example used as a reaction medium when using inorganic acid binders.

The sulfonic acid chlorides $R^1$—SO$_2$Cl are commercially available or can be produced according to processes known in the literature ("Methoden der Organischen Chemie" (Houben-Weyl), Thieme Verlag, Stuttgart 1955, p. 429: F. Muth, "Aromatische Sulfonsäuren").

Compounds of the general formula VII are obtained from compounds of the general formula VIII $$R^6-\underset{Me}{\overset{}{\bigcirc}}-O-R^5 \quad VIII$$

in which $R^5$ has the meanings given above and $R^6$ is a protected amino group. Protected amino groups are preferably understood as a benzyloxycarbonylamino group —NH—CO$_2$CH$_2$Ph, a tert.butyloxycarbonylamino group —NH—CO$_2$-t.Bu or a phthalimido group. The amino group or hydroxy group is released in a well-known manner. The benzyloxycarbonylamino group is converted into a free amino group by hydrogenation in the presence of a catalyst such as Raney nickel or palladium on carbon or by an acid such as concentrated formic acid, hydrochloric acid or hydrogen bromide in glacial acetic acid. A tert. butyloxycarbonylamino group is converted into an amino group by an acid such as hydrochloric acid in dioxane, formic acid or trifluoroacetic acid. A phthalimido group is converted into an amino group by an acid such as hydrochloric acid or by a base such as sodium hydroxide solution or potassium hydroxide solution or by the action of hydrazine hydrate.

Compounds of the general formula VIII are produced by reacting phenols of the general formula IX with compounds of the general formula X.

$$R^6-\underset{Me}{\overset{}{\bigcirc}}-OH \quad (IX) \qquad +R^7-CH_2-R^8 \quad (X)$$

$R^6$ in compounds of the general formula IX denotes a protected amino group such as a benzyloxycarbonylamino group —NH—CO$_2$CH$_2$Ph, a tert.-butyloxycarbonylamino group —NH—CO$_2$-t.Bu or a phthalimido group. $R^8$ in compounds of the general formula X has the same meanings as $R^5$ (nitrile, amide or phthalimidomethyl group) and a carboxylic ester group. $R^7$ denotes a chlorine, bromine or iodine atom or a hydroxy or arylsulfonyloxy group. If $R^7$ is a chlorine, bromine or iodine atom or an arylsulfonyloxy group, the reaction is preferably carried out in a solvent such as acetone, ether, toluene or dimethylformamide at temperatures between −30° C. and 100° C. preferably in the presence of a base such as sodium hydride or potassium carbonate. If $R^7$ is a hydroxy group the reaction is carried out in an inert solvent in the presence of diazodicarboxylic acid diethyl ester or diazodicarboxylic acid dipiperidide and triphenylphosphine. If $R^8$ in the general formula IX is a carboxylic ester group then this is now saponified preferably by potassium hydroxide in methanol and then converted into an amide group $CONH_2$ using ammonia. This conversion can also be carried out directly without prior saponification with the aid of $CH_3Al(Cl)NH_2$ which is prepared from trimethylaluminium and ammonium chloride.

Compounds of the general formula IX are produced by converting 3-amino-5-methyl-phenol (F. Wessely, H. Eibel, G. Friedrich, "Monatshefte Chem." 83, 24–30 (1952)) using anhydrides such as phthalic acid anhydride or BOC anhydride (tert. butyloxycarboxylic acid anhydride) or with benzyloxycarbonyl chloride. Compounds of the general formula X are commercially available.

A further preferred process for the production of compounds of the general formula III is to react compounds of the general formula XI

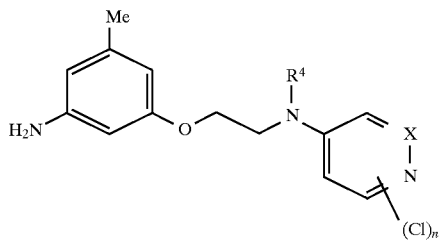

(XI)

in which $R^4$, X and n have the meanings stated above with sulfonic acid chlorides $R^1SO_2Cl$ in which $R^1$ has the meanings given above. It is expedient to carry out the reaction with the addition of an acid-binding agent such as alkali acetate, alkali hydroxide, calcium oxide, calcium carbonate, magnesium carbonate or with organic bases such as pyridine, triethylamine, N-methyl-morpholine or di-isopropylethylamine in which for example ether, methylene chloride, dioxane, toluene or an excess of the tertiary amine serves as the inert solvent. When inorganic acid binders are used water or aqueous ethanol is for example used as the reaction medium.

Compounds of the general formula XI are prepared from compounds of the general formula XII

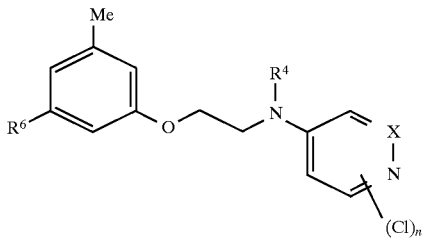

(XII)

in which $R^4$, $R^6$, X and n have the meanings given above. The amino group is released in a well-known manner. The benzyloxycarbonylamino group is converted into a free amino group by hydrogenation in the presence of a catalyst such as Raney nickel or palladium on carbon or by an acid such as concentrated formic acid, hydrochloric acid or with hydrogen bromide in glacial acetic acid. The tert. butyloxycarbonylamino group is converted into an amino group by an acid such as hydrochloric acid in dioxane, formic acid or trifluoroacetic acid. The phthalimido group is converted into an amino group by an acid such as hydrochloric acid or by a base such as sodium hydroxide solution or potassium hydroxide solution or by the action of hydrazine hydrate.

Compounds of the general formula XII are obtained by reacting compounds of the general formula IX with compounds of the general formula XIII.

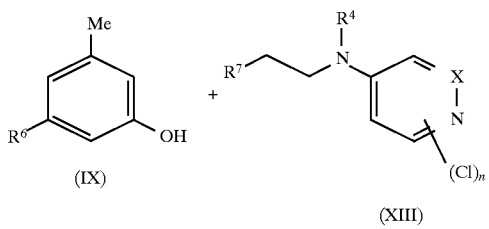

(IX)    (XIII)

$R^6$ in the general formula IX has the meanings stated above. $R^4$, $R^7$, X and n in the general formula XIII have the meanings given above. If $R^7$ is a chlorine, bromine or iodine atom or an arylsulfonyloxy group, the reaction is preferably carried out in a solvent such as acetone, ether, toluene or dimethylformamide at temperatures between −30° C. and 100° C. preferably in the presence of a base such as sodium hydride or potassium carbonate. If $R^7$ is a hydroxy group, the reaction is carried out in an inert solvent in the presence of diazodicarboxylic acid diethyl ester or diazodicarboxylic acid dipiperidide and triphenyl phosphine.

Compounds of the general formula XIII are obtained by reacting ethanolamine with pentachloropyridine or 4-nitrotetrachloropyridine (if X denotes a —CH group) or with 3,4,5-trichloropyridazine (if X denotes a nitrogen atom). This reaction is carried out in an inert solvent such as ethanol, toluene, tetrahydrofuran or dimethylformamide at temperatures between 0° and 100° C. in the presence of a base such as triethylamine, N-methyl-morpholine or potassium carbonate. In this process those compounds of the general formula XIII are firstly formed in which $R^7$ denotes a hydroxy group and $R^4$ denotes a hydrogen atom. If desired $R^4$ can then be converted into a benzyl group by acetylating the hydroxy group then reacting with benzyl bromide or benzyl chloride and cleaving the acetyl group off again. The hydroxy group can then be converted into a toluene-4-sulfonyloxy group or into a halogen atom if desired. This is achieved by reacting with toluene-4-sulfonyl chloride, thionyl chloride or thionyl bromide.

Examples of salts of compounds of formula I which can be used physiologically are salts with physiologically tolerated mineral acids such as hydrochloric acid, sulphuric acid, sulphurous acid or phosphoric acid, or with organic acids such as methanesulfonic acid, p-toluenesulfonic acid, acetic acid, trifluoroacetic acid, citric acid, fumaric acid, maleic acid, tartaric acid, succinic acid or salicylic acid. The compounds of formula I with a free carboxy group can also form salts with physiologically tolerated bases. Examples of such salts are alkaline metal, alkaline-earth metal, ammonium and alkylammonium salts such as a sodium, potassium, calcium or tetramethylammonium salt.

The compounds of formula I can be solvated and in particular hydrated. The hydrogenation can be achieved in the course of the production process or gradually occur as a result of hygroscopic properties of a compound of formula I which is firstly anhydrous.

Pure enantiomers of compounds of formula I can either be obtained by racemate resolution (by formation of salts with optically active acids or bases) or by using optically active starting materials in the synthesis.

For the production of pharmaceutical agents, the substances of the general formula I are mixed with suitable pharmaceutical carrier substances, aromatics, flavourings and dyes and are for example formed into tablets or dragees or are suspended or dissolved in water or oil e.g. olive oil with the addition of appropriate auxiliary substances.

The substances of the general formula I and their salts can be administered enterally or parenterally in a liquid or solid form. Water is preferably used as an injection medium which contains the usual additives in injection solutions such as stabilizers, solubilizers or buffers. Such additives are e.g. tartrate and citrate buffer, complexing agents (such as ethylenediaminetetraacetic acid and their non-toxic salts) and high molecular polymers such as liquid polyethylene oxide in order to regulate viscosity. Solid carrier materials are e.g. starch, lactose, mannitol, methylcellulose, talcum, highly dispersed silicic acids, high molecular fatty acids (such as stearic acid), animal and vegetable fats and solid high molecular polymers (such as polyethylene glycols). Preparations suitable for oral administration can, if desired, contain flavourings and sweeteners.

The compounds are usually administered in amounts of 10–1500 mg per day in relation to 75 kg body weight. It is preferable to administer 1–2 tablets with a content of active substance of 5–500 mg, 2–3 times per day. The tablets can also be retarded as a result of which only 1–2 tablets with 20–700 mg active substance have to be administered per day. The active substance can also be administered by injection 1–8 times per day or by continuous infusion in which case 50–2000 mg per day are usually sufficient.

The following compounds are preferred within the sense of the invention in addition to those mentioned in the examples:

1. N-(Dimethyloxophosphinylmethyl)-N-{3-methyl-5-[2-(pyridin-4-ylamino)-ethoxy]-phenyl}-2-ethoxy-benzenesulfonamide
2. N-(Dimethyloxophosphinylmethyl)-N-{3-methyl-5-[2-(pyridin-4-ylamino)-ethoxy]-phenyl}-2-propyloxy-benzenesulfonamide
3. N-(Dimethyloxophosphinylmethyl)-N-{3-methyl-5-[2-(pyridin-4-ylamino)-ethoxy]-phenyl}-2-(2-propyloxy)-benzenesulfonamide
5. N-(Dimethyloxophosphinylmethyl)-N-{3-methyl-5-[2-(pyridin-4-ylamino)-ethoxy]-phenyl}-2-pentyloxy-benzenesulfonamide Example 1

N-(Dimethyloxophosphinylmethyl)-N-{3-methyl-5-[2-(pyridin-4-ylamino)-ethoxyl]-phenyl}-benzene sulfonamide a) 36.0 g (292 mmol) 3-hydroxy-5-methyl-aniline (F. Wessely, H. Eibel, G. Friedrich, "Monatshefte Chem." 83, 24–30, (1952)) and 73.5 g (496 mmol) phthalic acid anhydride were heated for 2 hours under reflux to boiling in 280 ml glacial acetic acid. Water was added, it was heated for a short time, allowed to cool and filtered. 59.6 g (80%) 2-(3-hydroxy-5-methyl-phenyl)-isoindole-1,3-dione of Fp. 174°–175° C. was obtained.

b) 138 ml (2.5 mol) ethanolamine was added dropwise within 15 min to a suspension of 230 g (915 mmol) pentachloropyridine in 3.2 l dry dimethylformamide while cooling on ice, it was stirred for 30 min while cooling on ice and for 3 h at room temperature. The solvent was removed to a large extent, the remainder was poured onto 4 l ice water, filtered and the residue was crystallized from 800 ml dichloromethane. 172 g (69%) 2-(2,3,5,6-tetrachloropyridin-4-ylamino)-ethanol of Fp. 128°–130° C. was obtained.

c) A solution of 34.4 ml (490 mmol) acetyl chloride in 250 ml glacial acetic acid was added dropwise to a suspension of 105 g (380 mmol) 2-(2,3,5,6-tetrachloropyridin-4-ylamino)-ethanol in 860 ml glacial acetic acid. During this the temperature increased to 40° C. After 2 h it was poured onto ice water, filtered, washed with water, the residue was dissolved in 500 ml ethyl acetate, dried over sodium sulfate, filtered and the solvent was removed in a vacuum. 112 g (93%) acetic acid-2(2,3,5,6-tetrachloropyridin-4-ylamino)-ethyl ester was obtained and was reacted without further purification. MS (m/e)=316.

d) A solution of 111 g (350 mmol) acetic acid-2-(2,3,5,6-tetrachloropyridin-4-ylamino)-ethyl ester in 500 ml dimethylformamide was added dropwise at 10° C. within 10 min to a suspension of 11.5 g (455mmol) sodium hydride (95%) in 200 ml dimethylformamide. After 1 hour 54 ml (455 mmol) benzyl bromide was added dropwise within 10 min while cooling on ice. After 2 hours at room temperature 50 ml isopropanol was added and after 30 min it was poured onto 7 l ice water. It was filtered, the residue was dissolved in ethyl acetate, dried over sodium sulfate, filtered and the solvent was removed in a vacuum. It was digested with ether and 73.8 g (52%) acetic acid-2-[benzyl-(2,3,5,6-tetrachloropyridin-4-yl)-amino]ethyl ester of Fp. 98°–100° C. was obtained.

e) 187 g (436 mmol) acetic acid-2-[benzyl-(2,3,5,6-tetrachloropyridin-4-yl)-amino]-ethyl ester, 850 ml dimethylformamide, 2.1 l ethanol and 680 ml 2N sodium hydroxide solution were stirred for 2 h at room temperature, the solvent was removed in a vacuum to a large extent, the residue was dissolved in 1 l ethyl acetate, extracted twice with 3 l water, the organic phase was dried over sodium sulfate, filtered, the solvent was removed in a vacuum, the residue was digested with a small amount of diisopropyl ether, isohexane was added and it was allowed to crystallize. It was filtered, washed with isohexane and 140 g (84%) 2-[benzyl-(2,3,5,6-tetrachloropyridin-4-yl)-amino]-ethanol of Fp. 79°–81° C. was obtained.

f) 31.5 g (165 mmol) toluene-4-sulfonylchloride in 100 ml dichloromethane was added dropwise to 50.4 g (138 mmol) 2-[benzyl-(2,3,5,6-tetrachloropyridin-4yl)-amino]-ethanol and 34.4 ml triethylamine in 600 ml dry dichloromethane while cooling on ice and it was stored for 14 h at 5° C. It was extracted with water, the organic phase was dried with sodium sulfate, filtered, the solvent was removed in a vacuum, the residue was digested with methanol, filtered and 58.0 g (81%) toluene-4-sulfonic acid-2-[benzyl-(2,3,5,6-tetrachloropyridin-4-yl)-amino]-ethyl ester of Fp. 114°–116° C. was obtained.

g) A solution of 24.3 g (96 mmol) 2-(3-hydroxy-5-methyl-phenyl)-isoindole-1,3-dione in 200 ml dimethylformamide was added dropwise to 3.8 g (150 mmol) sodium hydride (95%) in 400 ml dimethylformamide while cooling on ice. After 30 min this solution was added dropwise to 50 g (96 mmol) toluene-4-sulfonic acid-2-[benzyl-(2,3,5,6-tetrachloropyridin-4-yl)-amino]-ethyl ester in 360 ml dimethylformamide. After 1 h it was poured onto ice water, extracted three times with ethyl acetate, the organic phase was extracted five times with water, the organic phase was dried over sodium sulfate, filtered, the solvent was removed in a vacuum and 50.4 g of an oily residue was obtained which was purified over a silica gel column (mobile solvent isohexane: ethyl acetate=9:1 to 7:3). 19.0 g (33%) 2-(3-{2-[benzyl-(2,3,5,6-tetrachloropyridin-4-yl)-amino]-ethoxy}-5-methyl-phenyl)-isoindole-1,3-dione of Fp. 142°–143° C. was obtained.

h) 61.4 g (100 mmol) 2-(3-{2-[benzyl-(2,3,5,6-tetrachloropyridin-4-yl)-amino]-ethoxy}-5-methyl phenyl)-isoindole-1,3-dione and 7.2 ml (150 mmol) hydrazine hydrate in 320 ml dichloromethane and 160 ml ethanol were stirred for 3 d at room temperature. 40 ml concentrated hydrochloric acid was added while cooling on ice, the crystal pulp was diluted with ethanol, stirred for 1 h, the solvent was removed in a vacuum, the residue was suspended in 2N sodium hydroxide solution, dichloromethane was added, it was stirred for 30 min, filtered, the organic phase was removed, the aqueous phase was extracted with dichloromethane, the combined organic phases were washed with water, the solvent was removed in a vacuum, the residue was digested with methanol and 37.6 g (78%) [2-(3-amino-5-methyl-phenoxy)-ethyl]-benzyl-(2,3,5,6-tetrachloropyridin-4-yl)-amine of Fp. 92°–93° C. was obtained.

i) 3.5 ml (27 mmol) benzenesulfonyl chloride was added dropwise to 11.5 g (25.5 mmol) [2-(3-amino-5-methyl-phenoxy)-ethyl]-benzyl-(2,3,5,6-tetrachloro- pyridin-4-yl)-amine in 55 ml pyridine while cooling on ice. After 1 h it was poured onto ice which had been admixed with 130 ml 6N hydrochloric acid, it was extracted with ethyl acetate, dried over sodium sulfate, filtered, the solvent was removed in a vacuum, the residue was digested with 100 ml ether/ di-isopropyl ether (1.1) and 13.7 g (91%) N-(3-{2-[benzyl-(2,3,5,6-tetrachloropyridin-4-yl)-amino]-ethoxy}-5-methyl-phenyl)-benzenesulfonamide of Fp. 147°–149° C. was obtained.

j) 1.0 g N-(3-{2-[benzyl-(2,3,5,6-tetrachloropyridin-4-yl)-amino]-ethoxy}-5-methyl-phenyl)-benzene-sulfonamide, 0.62 g chloromethyldimethyl phosphanoxide and 0.68 g potassium carbonate were stirred for 20 min. at 150°–160° C., it was extracted with methanol, filtered, the solvent was removed in a vacuum, the residue was digested with a mixture of ethyl acetate and methanol (9:1), filtered, purified on a silica gel column (mobile solvent/methanol= 9:1), the solvent was removed in a vacuum and 1.0 g (N-(3-{2-[benzyl-(2,3,5,6-tetrachloropyridin-4-yl)-amino]-ethoxy}-5-methyl-phenyl)-N-(dimethyloxophosphinyl-methyl)-benzenesulfonamide was obtained as an amorphous mass. MS (m/e)=701.

k) 1.0 g (1.4 mmol) N-(3-{2-[benzyl(2,3,5,6-tetrachloropyridin-4-yl)-amino]-ethoxy}-5-methyl-phenyl)-N-(dimethyloxophosphinyl-methyl)-benzenesulfonamide, 1.15 ml 1,3,5-trimethylbenzene and 8 ml trifluoroacetic acid were stirred for 12 h at room temperature, poured onto 150 ml water, made alkaline with concentrated aqueous ammonia solution, filtered, washed with water and ether, the residue was dissolved in ethyl acetate, dried over sodium sulfate, treated with kieselguhr, filtered, the solvent was removed in a vacuum, the residue was taken up in 3 ml ethyl acetate, admixed with 30 ml ether and allowed to crystallize. It was filtered and 0.5 g (58%) N-(dimethyloxophosphinyl-methyl)-N-{3-methyl-5-[2-(2,3,5,6)-tetrachloropyridin-4-ylamino)-ethoxy]-phenyl}-benzenesulfonamide of Fp. 152°–154° C. was obtained.

l) 0.2 g (0.33 mmol) N-(dimethyloxophosphinyl-methyl)-N-{3-methyl-5-[2-(2,3,5,6-tetrachloropyridin-4-ylamino)-ethoxy]-phenyl}-benzenesulfonamide in 10 ml methanol was hydrogenated in the presence of 0.28 ml triethylamine and 0.1 g 10% palladium on carbon at room temperature and normal pressure. After 18 hours it was filtered, the residue was dissolved in 3 ml ethanol, 30 ml ether was added, it was filtered, washed with ether and 0.12 g (77%) of the title compound of Fp. 228°–232° C. was obtained.

EXAMPLE 2

N-(Dimethyloxophosphinvlmethyl)-N-{3-methyl-5-[2-(pyridin-4-ylamino)-ethoxyl]-phenyl}-2-methoxy-benzene-sulfonamide was obtained in a 24% yield analogously to example 1 wherein in step 1i) 2-methoxy-benzenesulfonyl chloride was used instead of benzenesulfonyl chloride. Amorphous. MS (m/e)=503.

EXAMPLE 3

N-(Dimethyloxophosphinylmethyl)-N-{3-methyl-5-[2-(pyridin-4-ylamino)-ethoxyl]-phenyl}-2-butoxy-benzene-sulfonamide was obtained in a 10% yield analogously to example 1 wherein in step 1i) 2-butoxy-benzenesulfonyl chloride was used instead of benzenesulfonyl chloride. Amorphous. MS (m/e)=545.

EXAMPLE 4

N-(Dimethyloxophosphinylmethyl)-N-{3-methyl-5-[2-(pyridin-4-ylamino)-ethoxyl]-phenyl}-2-hexyloxy-benzene-sulfonamide was obtained in a 20% yield analogously to example 1 wherein in step 1i) 2-hexyloxy-benzenesulfonyl chloride was used instead of benzenesulfonyl chloride. Amorphous. MS (m/e)=573.

EXAMPLE 5

N-(Dimethyloxophosphinvlmethyl)-N-{3-methyl-5-[2-(pyridin-4-ylamino)-ethoxyl]-phenyl}-2-methoxy-benzene-sulfonamide a) 59 g (233 mmol) 2-(3-hydroxy-5-methyl-phenyl)-isoindole-1,3-dione, 44 ml (700 mmol) chloroacetonitrile and 96.7 g (700 mmol) potassium carbonate were heated for 4 h to 80° C. in 300 ml dry dimethylformamide. It was poured onto 2 l water, filtered and 60.5 g (89%) [3-(1,3-dioxo-1,3-dihydro-isoindole-2-yl)-5-methyl-phenoxy]-acetonitrile of Fp. 156°–157° C. was obtained.

b) 30.0 g (103 mmol) [3-(1,3-dioxo-1,3-dihydro-isoindole-2-yl)-5-methyl-phenoxy]-acetonitrile and 6.0 ml (123 mmol) hydrazine hydrate in 500 ml ethanol were stirred for 4 h at room temperature, the precipitate was suction filtered, digested with ether and 16.7 g (quant.) (3-amino-5-methyl-phenoxy)-acetonitrile of Fp. 76°–77° C. was obtained.

c) 11.4 g (55 mmol) 2-methoxy-benzenesulfonyl chloride was added in portions at 10° C. to 8.9 g (55 mmol) (3-amino-5-methyl-phenoxy)-acetonitrile and 7.6 ml (55 mmol) triethylamine in 70 ml dichloromethane, it was stirred for 1 h at room temperature, extracted with water, the organic phase was dried over sodium sulfate, filtered, the solvent was removed in a vacuum, the residue was digested with ether and 8.5 g (46%) N-(3-cyanomethoxy-5-methyl-phenyl)-2-methoxy-benzenesulfonamide of Fp. 156°–157° C. was obtained.

d) 5.0 g (15 mmol) N-(3-cyanomethoxy-5-methyl-phenyl)-2-methoxy-benzenesulfonamide, 9.5 g (75 mmol)

chloromethyl-dimethyl-phosphanoxide and 10.5 g (75 mmol) potassium carbonate were stirred for 30 min at 160° C. It was extracted with ethyl acetate, filtered over silica gel (ethyl acetate:glacial acetic acid 95:5), about ⅔ of the solvent was removed, it was extracted with sodium hydrogen carbonate, the ethyl acetate phase was dried over sodium sulfate, filtered, the solvent was removed in a vacuum and 5.0 g (79%) N-(dimethyloxophosphinyl-methyl)-N-(3-cyanomethoxy-5-methyl-phenyl)-2-methoxy-benzenesulfonamide was obtained as colourless crystals of Fp. 143–145° C.

e) 3.3 ml Chlorotrimethylsilane was added dropwise under nitrogen and while cooling on ice to 0.29 g (13.2 mmol) lithium borohydride in 5 ml tetrahydrofuran, it was stirred for 1 h at room temperature, a solution of 0.93 g (2.2 mmol) N-(dimethyloxophosphinyl-methyl)-N-(3-cyanomethoxy-5-methyl-phenyl)-2-methoxy-benzenesulfonamide in 5 ml tetrahydrofuran was added dropwise, it was stirred for 1 h at room temperature, water was added dropwise, the solvent was removed in a vacuum, it was taken up in a small amount of dichloromethane and filtered over silica gel (dichloromethane:methanol=9:1), the solvent was removed in a vacuum and 900 mg (91%) N-(dimethyloxophosphinyl-methyl)-N-[3-(2-amino-ethoxy)-5-methyl-phenyl]-2-methoxy-benzenesulfonamide was obtained as an oil. MS (m/e)=426.

f) 940 mg N-(dimethyloxophosphinyl-methyl)-N-[3-(2-amino-ethoxy)-5-methyl-phenyl]-2-methoxy-benzene sulfonamide, 400 mg (2.2 mmol) 3,4,5-trichloropyridazine and 0.31 ml (2.2 mmol) triethylamine in 20 ml dry tetrahydrofuran were stirred for 2 h at 80° C., the solvent was removed in a vacuum, the residue was stirred with water, extracted three times with ethyl acetate, dried over sodium sulfate, filtered, the solvent was removed in a vacuum and 1.26 g (quant.) of a mixture of N-(dimethyloxophosphinyl-methyl)-N-{3-[2-(3,5-dichloropyridazin-4-ylamino)-ethoxy]-5-methylphenyl-}-2-methoxy-benzenesulfonamide and N-(dimethyloxophosphinyl-methyl)-N-{3-[2-(3,4-dichloropyridazin-5-ylamino)-ethoxy]-5-methylphenyl}-2-methoxy-benzenesulfonamide was obtained as an oil. MS (m/e)=573.

g) 1.3 g (2.2 mmol) of this mixture and 0.9 g (6.6 mmol) potassium carbonate in 80 ml methanol was hydrogenated in the presence of 0.3 g 10% palladium on carbon at room temperature and normal pressure. It was filtered over silica gel, the solvent was removed in a vacuum and 415 mg (38%) of the title compound was obtained as an oil. MS (m/e)=504.

EXAMPLE 6

N-(Dimethyloxophosphinyl-methyl)-N-{3-methyl-5-[2-(pyridin-4-ylamino)-ethoxy]-phenyl}-2-propyloxy-benzenesulfonamide was produced analogously to example 5 in a 33% yield. Oil. MS (m/e)=532. For this 2-propyloxy-benzene-sulfonyl chloride was used in step 5c) instead of 2-methoxy-benzenesulfonyl chloride and one obtained N-(3cyanomethoxy-5-methyl-phenyl)-2-propyloxy-benzene-sulfonamide (Fp. 154°–155° C.) in a 57% yield, which was reacted to N-(dimethyloxo-phosphinyl-methyl)-N-(3-cyanomethoxy-5-methyl-phenyl)-2-propyloxy-benzene-sulfonamide (60% yield, Fp. 143°–145° C.) analogously to example 5d), which was reacted analogously to example 5e) to form N-(dimethyloxophosphinyl-methyl)-N-[3-(2-amino-ethoxy)-5-methyl-phenyl]-2-propyloxy-benzene-sulfonamide (86% yield, oil, MS (m/e)=454), which was reacted analogously to example 5f) to form a mixture of N-(dimethyloxophosphinyl-methyl)-N-{3-[2-(3,5-dichloropyridazin-4-ylamino)-ethoxy]-5-methyl-phenyl}-2-propyloxy-benzenesulfonamide and N-(dimethyloxophosphinyl-methyl)-N-{3-[2-(3,4-dichloropyridazin-5-ylamino)-ethoxy]-5-methyl-phenyl}-2-propyloxy-benzenesulfonamide (quant., oil, MS (m/e)=601) from which the title compound was obtained by catalytic hydrogenation analogously to example 5g).

EXAMPLE 7

N-(Dimethyloxophosphinyl-methyl)-N-{3-methyl-5-[2-(pyridin-4-ylamino)-ethoxyl]-phenyl}-2-ethoxy-benzene-sulfonamide was produced in a 54% yield analogously to example 5. Oil. MS (m/e)=518. For this 2-ethoxy-benzenesulfonyl chloride is used in step 5c) instead of 2-methoxy-benzenesulfonyl chloride and one obtained N-(3-cyanomethoxy-5-methyl-phenyl)-2-ethoxy-benzenesulfonamide in a 70% yield (Fp. 142° C.) which was reacted analogously to example 5d) to form N-(dimethyloxophosphinyl-methyl)-N-(3-cyanomethoxy-5-methyl-phenyl)-2-ethoxy-benzene-sulfonamide (46% yield, Fp. 139°–141° C.) and this was reacted analogously to example 5e) to form N-(dimethyloxophosphinyl-methyl)-N-[3-(2-amino-ethoxy)-5-methyl-phenyl]-2-ethoxy-benzenesulfonamide (58% yield, oil, MS (m/e)=440) which was reacted analogously to example 5f) to form a mixture of N-(dimethyloxophosphinylmethyl)-N-{3-[2-(3,5-dichloropyridazin-4-ylamino)-ethoxy]-5-methyl-phenyl}-2-ethoxy-benzenesulfonamide and N-(dimethyloxophosphinyl-methyl)-N-{3-[2-(3,4-dichloropyridazin-5-ylamino)-ethoxy]-5-methyl-phenyl}-2-ethoxy- benzenesulfonamide (55%, Fp. 114°–116° C.) from which the title compound was obtained analogously to example 5g) by catalytic hydrogenation.

EXAMPLE 8

N-(Dimethyloxophosphinyl-methyl)-N-{3-methyl-5-[2-(pyridin-4-ylamino)-ethoxyl]-phenyl}-2-(2-propyl-oxy)-benzenesulfonamide was produced in a 35% yield analogously to example 5. Oil. MS (m/e)=532. For this 2-isopropyloxy-benzene-sulfonyl chloride was used in step 5c) instead of 2-methoxy-benzenesulfonyl chloride and N-(3-cyanomethoxy-5-methyl-phenyl)-2-(2-propyloxy)-benzenesulfonamide (Fp. 100°–102° C.) was obtained in a 21% yield which was reacted analogously to example 5d) to form N-(dimethyloxophosphinyl-methyl)-N-(3-cyanomethoxy-5-methyl-phenyl)-2-(2-propyloxy)-benzenesulfonamide (65% Fp. 137°–140° C.) and this was reacted analogously to example 5e) to form N-(dimethyloxophosphinyl-methyl)-N-[3-(2-amino-ethoxy)-5-methyl-phenyl]-2-(2-propyloxy)-benzene sulfonamide (75% oil, MS (m/e)=454) which was reacted analogously to example 5f) to form a mixture of N-(dimethyloxophosphinyl-methyl)-N-{3-[2-(3,5-dichloro-pyridin-4-ylamino)-ethoxy]-5-methyl-phenyl}-2-(2-propyloxy)-benzenesulfonamide and N-(dimethyloxo-phosphinyl-methyl)-N-{3-[2-(3,4-dichloro-pyridin-5-ylamino)-ethoxy]5-methyl-phenyl}-2-(2-propyloxy)-benzenesulfonamide (quant., oil, MS (m/e)=601) from which the title compound was obtained analogously to example 5g) by catalytic hydrogenation.

EXAMPLE 9

N-(Dimethyloxophosphinyl-methyl)-N-{3-methyl-5-[2-(pyradazin-4-ylamino)-ethoxyl]-phenyl}-2-butoxy-benzene-sulfonamide was produced in a 41% yield analogously to example 5. Oil. MS (m/e)=. For this 2-butoxy-benzenesulfonyl chloride was used in step 5c) instead of 2-methoxy-benzenesulfonyl chloride and N-(3-cyanomethoxy-5-methyl-phenyl)-2-ethoxy-benzenesulfonamide (Fp. 121°–123° C.) was obtained in a 96% yield was obtained which was reacted analogously to example 5d) to form N-(dimethyloxophosphinyl-methyl)-N-(3-cyanomethoxy-5-methyl-phenyl)-2-butoxy-benzenesulfonamide (43% yield, Fp. 151°–152° C.) and this was reacted analogously to example 5e) to form N-(dimethyloxophosphinyl-methyl)-N-[3-(2-amino-ethoxy)-5-methyl-phenyl]-2-butoxy-benzenesulfonamide (67% yield, oil, MS (m/e)=468) which was reacted analogously to example 5f) to form a mixture of N-(dimethyloxophosphinyl-methyl)-N-{3-[2-(3,4-dichloropyridazin-4-ylamino)-ethoxy]-5-methyl-phenyl}-2-butoxy-benzenesulfonamide and N-(dimethyloxo-phosphinyl-methyl)-N-{3-[2-(3,4-dichloropyridazin-5-ylamino)-ethoxy]-5-methyl-phenyl}-2-butoxy-benzenesulfonamide (quant, oil, MS (m/e)=615) from which the title compound was obtained analogously to example 5g) by catalytic hydrogenation.

EXAMPLE 10

Thrombin time

A conventional test in clinical coagulation diagnostics is the thrombin time. This parameter measures the action of thrombin on fibrinogen and the formation of clots. Inhibitors of thrombin result in an extended thrombin time.

In order to obtain plasma 9 parts of fresh blood from healthy donors was mixed with one part of sodium citrate solution (0.11 mol/l) and it was centrifuged for 10 minutes at room temperature at ca. 3000 r.p.m. The plasma was removed by pipette and can be stored at room temperature for ca. 8 hours.

200 µl citrate plasma was incubated for 2 minutes at 37° C. in a ball coagulometer (KC10 from the Amelung Company). 10 µl dimethylsulfoxide (DMSO) or a solution of the active substance in DMSO was added to 190 µl pre-heated thrombin reagent (Boehringer Mannheim GmbH; contains ca. 3 U/ml horse thrombin and 0.0125M Ca$^{++}$). On addition of 200 µl of this solution to the plasma a stopwatch was started and the time at which coagulation starts was determined. The thrombin time was ca. 24 sec. in control measurements and was substantially increased by the active substances.

The measured thrombin times in seconds are given in the following table as a difference to the control. The concentrations of the active substances in human plasma were 5 µM (TT5) and 0.5 µM (TT0.5).

Thrombin inhibition

The kinetic measurements were carried out in 0.1M phosphate buffer that contained 0.2M sodium chloride and 0.5% polyethylene glycol 6000 at a pH=7.5 and 25° C. with the substrate H-(D)-Phe-Pro-Arg-pNA; Kabi and human α thrombin (Sigma, specific activity=2150 NIH-units/mg) in polystyrene semi-microcuvettes in a total volume of 1 ml.

In a preliminary test each active substance was determined as to whether it inhibits thrombin rapidly or slowly. For this the reaction was firstly started by adding 0.03 NIH units thrombin to a 100 µM solution of the substrate and the active substance. In a second experiment, substrate was added to a solution of thrombin and the active substance which had been incubated for 5 minutes. The increase in the concentration of p-nitroaniline with time was monitored spectroscopically (UV-VIS spectrophotometer Lambda-2 from the Perkin-Elmer Company) at 405 nm for 12 min.

Since the measured curves obtained in both experiments were linear and parallel, the active substances of the following table are rapid thrombin inhibitors.

The inhibition constants $K_i$ were then determined as follows. The substrate was used at concentrations of 100 µM, 50 µM, 30 µM, 20 µM and at each substrate concentration a measurement was carried out without inhibitor and three measurements were carried out in the presence of various concentrations of the inhibitors listed in the following table. The reactions were started by adding thrombin. The increase in absorbance at 405 nm due to the formation of p-nitroaniline was monitored over a time period of 12 minutes. Measurement points (time versus absorbance) were transferred to a PC at intervals of 20 seconds. The rates $V_O$ (change in absorbance per second; measurements without inhibitor) and $V_i$ (measurements with inhibitor) were determined by linear regression. Only that part of the measurement was used in which the substrate concentration had decreased by less than 15%. $K_m'$ and $V_{max}$ were determined from a measurement series (constant inhibitor concentration, variable substrate concentrations) by a non-linear fit to the equation $$V = \frac{V_{max}*[S]}{[S] + K_m'}$$

Finally $K_i$ was calculated from the entire series of measurements by a non-linear fit to the equation $$V = \frac{V_{max}*[S]}{K_m*(1 + [S]/K_i) + [S]}$$

The Michaelis constant $K_m$ was 3.8±2 µm in all measurements.

The inhibition constants $K_i$ of the active substances are stated in the following table in units of µM.

Inhibition of trypsin and plasmin 10 mg bovine pancreatic trypsin (Sigma) was dissolved in 100 ml 1 mM hydrochloric acid and stored in a refrigerator. 20 µl of this was admixed with 980 µl 1 mM hydrochloric acid. 25 µl thereof was used for each measurement. The measurement was carried out as described for thrombin. $K_m$=45 µM.

The measurements with human plasmin (Sigma, 10 units) were carried out as described for thrombin using the substrate S-2251 (H-(D)-Val-Leu-Lys-pNA, Kabi). 0.01 units plasmin were used for each measurement. $K_m$=250 µM.

| Compounds of example | TT5 | TT0.5 | $K_i$ [µM] thrombin |
|---|---|---|---|
| 1 | 175 | 33 | 0.100 |
| 2 | 300 | 115 | 0.008 |
| 3 | 300 | 50 | 0.004 |
| 4 | 113 | 11 | 0.012 |
| 5 | 162 | 32 | 0.042 |
| 6 | 122 | 18 | 0.028 |
| 7 | 109 | 14 | 0.060 |
| 8 | 180 | 47 | 0.035 |

A trypsin and plasmin inhibition was not found for the compounds according to the invention.

We claim:

1. A compound of the formula:

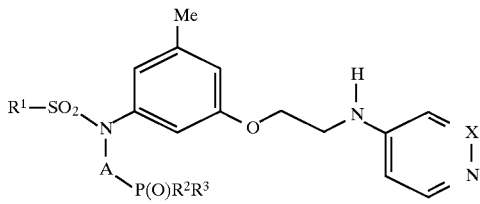

wherein
- $R^1$ is a group which is phenyl, naphthyl, furan, thiophene, pyrrole, oxazole, isoxazole, thiazole, isothiazole, imidazole, pyrazole, triazole, tetrazole, pyridine, pyridazine, benzothiophene, dibenzolhiophene, benzimidazole, carbazole, benzophuran, benzofurazan, benzo-2,1,3-thiadiazole, which group is unsubstituted or substituted at least once by at least one of nitro, halogen, nitrile, hydroxy, carboxy, $C_1-C_6$-alkoxycarbonyl, phenyl-$C_1-C_6$-alkoxycarbonyl, phenyl, $C_1-C_6$, alkyl, trifluoromethyl, $C_1-C_6$ alkoxy, $C_3-C_6$ alkenyloxy, $C_1-C_6$ alkinyloxy, benzyloxy, $C_1-C_6$ alkylthio, $C_1-C_6$ alkylsulfinyl, $C_1-C_6$ alkylsulfonyl, amino, $C_1-C_6$ alkylamino, di-$C_1-C_6$ alkylamino, benzylamino, bis(benzyl)amino, $C_1-C_6$ alkylsulfonylamino, $C_1-C_6$ alkylcarbonylamino, formylamino, carbamoyl, thiocarbamoyl, $C_1-C_6$ alkylaminocarbonyl, di-$C_1-C_6$-alkylaminocarbonyl or ethoxycarbonylmethoxy; and
- $R^2$ and $R_3$-are independently a straight-chain or-branched $C_1-C_6$ alkyl;
- A is a straight-chain or branched $C_1-C_6$ alkylene residue; and
- X is a CH group or a nitrogen atom; or an optically active form, racemate, diastersomer mixture, hydrate, solvate or physiologically acceptable salt thereof.

2. Compound of claim 1, wherein $R_1$ is an unsubstituted phenyl group or a phenyl group substituted by an $C_1-C_6$ alkoxy group.

3. Compound of claim 1, wherein $R^2$ and $R^3$ are the same.

4. Compound of claim 1, wherein X is a CH group.

5. Compound of claim 1, wherein X is a nitrogen atom.

6. Pharmaceutical composition suitable for the treatment of thromboembolic diseases comprising a compound of claim 1 and a pharmaceutically acceptable carrier.

7. A method of treating a thromboembolic disease in a patient in need of such treatment, said method comprising administering to said patient an effective amount of a compound of claim 1.

8. Compound of claim 1, wherein the compound is N-(dimethyloxophosphinylmethyl)-N-{3-methyl-5-[2-(pyridin-4-ylamino)-ethoxy]-phenyl}-2-methoxy-benzenesulfonamide.

9. Compound of claim 1, wherein the compound is N-(dimethyloxophosphinylmethyl)-N-{3-methyl-5-[2-(pyridin-4-ylamino)-ethoxy]-phenyl}2-methoxy-benzenesulfonamide.

10. Compound of claim 1, wherein the compound is N-(dimethyloxophosphinylmethyl)-N-{3-methyl-5-[2-(pyridin-4-ylamino)-ethoxy]-phenyl}-2-butoxy-benzenesulfonamide.

11. Compound of claim 1, wherein the compound is N-(dimethyloxophosphinylmethyl)-N-{3-methyl-5-[2-(pyridin-4-ylamino)-ethoxy]-phenyl}-2-hexyloxy-benzenesulfonamide.

12. Compound of claim 1, wherein the compound is N-(dimethyloxophosphinylmethyl)-N-{3-methyl-5-[2-(pyridin-4-ylamino)-ethoxy]-phenyl}-2-methoxy-benzenesulfonamide.

13. Compound of claim 1, wherein the compound is N-(dimethyloxophosphinylmethyl)-N-{3-methyl-5-[2-(pyridin-4-ylamino)-ethoxy]-phenyl}-2-propyloxy-benzenesulfonamide.

14. Compound of claim 1, wherein the compound is N-(dimethyloxophosphinylmethyl)-N-{3-methyl-5-[2-(pyridin-4-ylamino)-ethoxy]-phenyl}-2-ethoxy-benzenesulfonamide.

15. Compound of claim 1, wherein the compound is N-(dimethyloxophosphinylmethyl)-N-{3-methyl-5-[2-(pyridin-4-ylamino)-ethoxy]-phenyl}-2-(2-propyl-oxy)-benzenesulfonamide.

* * * * *